United States Patent [19]
Kumazawa et al.

[11] Patent Number: 6,150,355
[45] Date of Patent: Nov. 21, 2000

[54] PHENYLPIPERIDINE DERIVATIVE

[75] Inventors: Toshiaki Kumazawa; Hirokazu Koshimura; Shigeru Aono, all of Sunto-gun; Shunji Ichikawa, Tagata-gun; Shigeto Kitamura, Machida, all of Japan

[73] Assignee: Kyowa Hakko Kogyo Co., Ltd., Tokyo, Japan

[21] Appl. No.: 09/043,154

[22] PCT Filed: Sep. 11, 1996

[86] PCT No.: PCT/JP96/02589

§ 371 Date: Mar. 13, 1998

§ 102(e) Date: Mar. 13, 1998

[87] PCT Pub. No.: WO97/10213

PCT Pub. Date: Mar. 20, 1997

[30] Foreign Application Priority Data

Sep. 13, 1995 [JP] Japan ................................. 7-235022

[51] Int. Cl.[7] ...................... C07D 211/06; C07D 221/06; C07D 498/00; A01N 43/46; A01N 43/42
[52] U.S. Cl. ..................... 514/215; 514/217; 514/290; 514/291; 514/321; 514/323; 514/324; 514/325; 540/521; 540/522; 546/89; 546/93; 546/196; 546/198; 546/200; 546/202; 546/203
[58] Field of Search ................ 546/203, 89, 93, 546/198, 200, 202, 196; 514/215, 217, 290, 291, 321, 323, 324, 325; 540/521, 522

[56] References Cited

U.S. PATENT DOCUMENTS

| | | | |
|---|---|---|---|
| 4,882,351 | 11/1989 | Oshima et al. | 514/431 |
| 5,010,087 | 4/1991 | Oshima et al. | 514/307 |
| 5,010,104 | 4/1991 | Oshima et al. | 514/510 |
| 5,436,255 | 7/1995 | Butler | 514/320 |

FOREIGN PATENT DOCUMENTS 61-225167  10/1986  Japan .

OTHER PUBLICATIONS

European Journal of Pharmacology, vol. 43 (1977) 253–267.
European Journal of Pharmacology, vol. 72 (1981) 305–311.
Khim. Khim. Tekhnol, vol. 21 (1978) 810–812.

*Primary Examiner*—John Kight
*Assistant Examiner*—Raymond Covington
*Attorney, Agent, or Firm*—Fitzpatrick, Cella, Harper & Scinto

[57] ABSTRACT

A phenylpiperidine derivative or pharmaceutical acceptable salt thereof represented by formula (I):

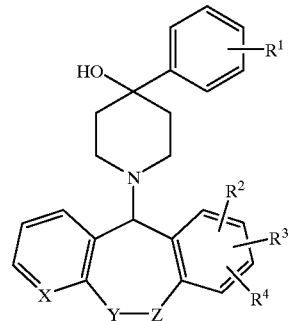

wherein X represents CH or N; Y—Z represents $CH_2$—O, $CH_2$—S, $CH_2$—$CH_2$, CH=CH or $CONR^5$ (wherein $R^5$ represents hydrogen or lower alkyl); $R^1$ represents hydrogen, lower alkyl, halogen, lower alkoxy or trifluoromethyl; and $R^2$, $R^3$ and $R^4$ are the same or different and each represents hydrogen, lower alkyl or $QR^6$ (wherein Q represents a single bond or lower alkylene, and $R^6$ represents hydroxy, lower alkoxyalkoxy, lower alkoxy, lower alkylthio, nitro, halogen, lower alkanoyloxy, lower alkoxycarbonyl, lower alkanoyl or carboxyl).

The present invention provides novel phenylpiperidine derivatives useful as analgesics.

22 Claims, No Drawings

PHENYLPIPERIDINE DERIVATIVE

TECHNICAL FIELD

The present invention relates to novel phenylpiperidine derivatives useful as analgesics.

BACKGROUND ART

Although nonsteroidal anti-inflammatory drugs, narcotic analgesics, and antagonistic analgesics are conventionally used as analgesics, there is demand for novel useful analgesics in which the adverse effects of these drugs are reduced.

As compounds having 4-hydroxy-4-phenylpiperidino group and analgesic action, the following compounds are known. For example, compounds represented by Formula (A) are reported in European Journal of Pharmacology, Vol. 43, p253, 1977.

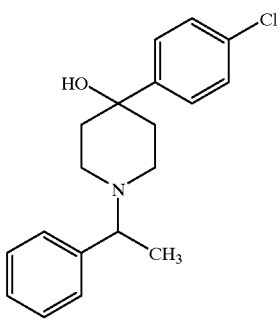

(A)

Also compounds represented by Formula (B) are reported in European Journal of Pharmacology, Vol. 72, p305, 1981.

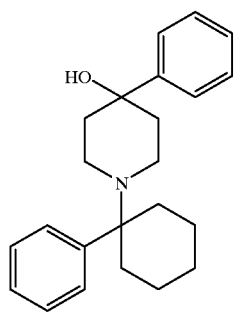

(B)

Further compounds (C) are reported in Lzv. Vyssh. Uchebn. Zarved., Khim. Khim. Teknol, Vol. 21, p810, 1978.

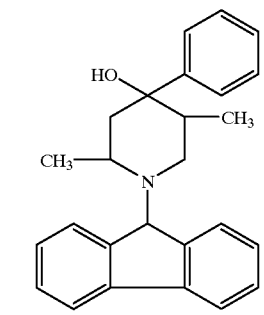

(C)

DISCLOSURE OF INVENTION

The present invention relates to phenylpiperidine derivatives or pharmaceutically acceptable salts thereof represented by formula (I):

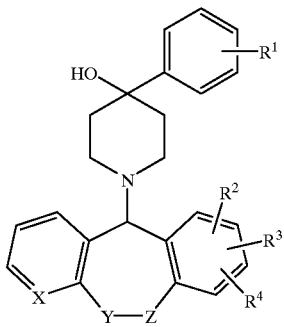

(I)

wherein X represents CH or N; Y-Z represents $CH_2$—O, $CH_2$—S, $CH_2$—$CH_2$, CH=CH or $CONR^5$ (wherein $R^5$ represents hydrogen or lower alkyl); $R^1$ represents hydrogen, lower alkyl, halogen, lower alkoxy or trifluoromethyl; and $R^2$, $R^3$ and $R^4$ are the same or different and each represents hydrogen, lower alkyl or $QR^6$ (wherein Q represents a single bond or lower alkylene; and $R^6$ represents hydroxy, lower alkoxyalkoxy, lower alkoxy, lower alkylthio, nitro, halogen, lower alkanoyloxy, lower alkoxycarbonyl, lower alkanoyl or carboxyl).

Hereinafter, compounds represented by formula (I) are referred to as compounds (I), and the same shall apply to compounds of other formula numbers.

In the definition of the groups in formula (I), lower alkyl and the lower alkyl moiety of lower alkoxy, lower alkoxyalkoxy, lower alkylthio and lower alkoxycarbonyl means a straight chain or branched alkyl group having 1 to 6 carbon atoms, such as methyl, ethyl, propyl, isopropyl, butyl, isobutyl, sec-butyl, tert-butyl, pentyl and hexyl. Lower alkylene and the alkylene moiety of lower alkoxyalkoxy means a bivalent saturated aliphatic group having 1 to 6 carbon atoms, such as methylene, ethylene, trimethylene, propylene, tetramethylene, butylene, pentamethylene, amylene, hexamethylene and hexylene. Lower alkanoyl and the lower alkanoyl moiety of lower alkanoyloxy may be a straight chain or branched alkanoyl group having 1 to 6 carbon atoms, such as formyl, acetyl, propionyl, butyryl, isobutylryl, valeryl and pivaloyl. Halogen means fluorine, chlorine, bromine or iodine.

Examples of the pharmaceutically acceptable salts of compounds (I) include inorganic acid addition salts such as hydrochloride, sulfate and phosphate; organic acid addition salts such as maleates, fumarates, oxalates, citrates and methanesulfonates; ammonium salt; lithium salt; sodium salt; potassium salt; magnesium salt; and calcium salt.

The process for producing compounds (I) are described below.

In the production process below, when the defined groups are changed under the process conditions or are unsuitable for carrying out the process, a desired compound can be obtained by using a method of introducing and eliminating protective groups, which is generally used in synthetic organic chemistry [refer to, for example, Protective Groups in Organic Synthesis, written by T. W. Green, John Wiley & Sons Inc. (1981)].

Production Process 1

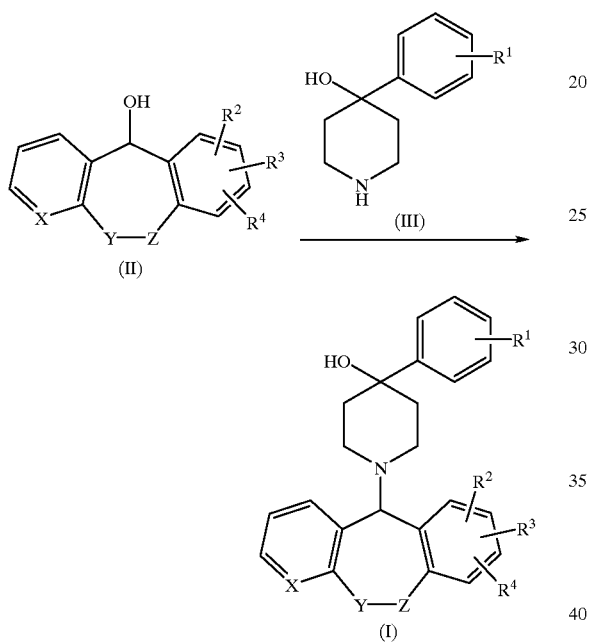

(wherein X, Y-Z, $R^1$, $R^2$, $R^3$ and $R^4$ are defined as described above).

Raw material compound (II) is obtained by the process disclosed in, for example, JP,A, 2-250 or in accordance with the process. Compound (III) is commercially available or obtained in accordance with the process described in Collect. Czech. Chem. Commun., Vol. 55, p1828, 1990.

Compound (II) is reacted with 1 to 10 equivalents of a halogenating agent such as thionyl chloride and phosphorus tribromide in a solvent such as methylene chloride and chloroform at an appropriate temperature between 0° C. to the boiling point of the used solvent for 30 minutes to 6 hours, if required, in the presence of 1 to 10 equivalents of base such as triethylamine and pyridine to give a corresponding halogenated product. The obtained halogenated product is reacted with 1 to 10 equivalents of compound (III) in a solvent such as methylene chloride and chloroform, if required, in the presence of 1 to 10 equivalents of base such as triethylamine and pyridine at an appropriate temperature between 0° C. to the boiling point of the used solvent for 30 minutes to 6 hours to give the desired compound (I).

Production Process 2

Compound (I) having various functional groups as $R^2$, $R^3$ and $R^4$ can also be obtained by a known process of transforming functional groups (for example, Comprehensive Organic Transformations, R. C. Larock, 1989). An example of such production process comprises the following steps:

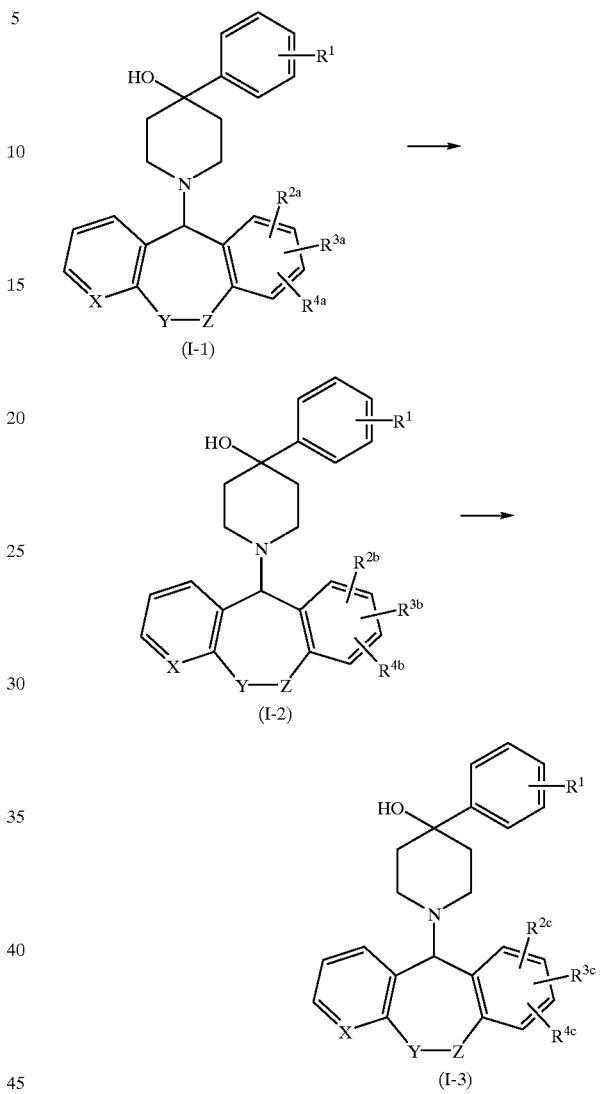

(wherein X, Y-Z and $R^1$ are defined as described above, at least one of $R^{2a}$, $R^{3a}$ and $R^{4a}$ is a group in which $R^6$ of the above $R^2$, $R^3$ and $R^4$ is lower alkoxycarbonyl, at least one of $R^{2b}$, $R^{3b}$ and $R^{4b}$ is a group in which $R^6$ of the above $R^2$, $R^3$ and $R^4$ is hydroxyl, and Q is lower alkylene, and at least one of $R^{2c}$, $R^{3c}$ and $R^{4c}$ is a group in which $R^6$ of the above $R^2$, $R^3$ and $R^4$ is formyl).

Compound (I-2) is obtained by treating Compound (I-1) with 1 to 10 equivalents of reducing agent such as lithium aluminum hydride in a solvent such as ether and tetrahydrofuran at an appropriate temperature between 0° C. to the boiling point of the solvent used.

Compoung (I-3) is obtained by treating Compound (I-2) with 1 to 10 equivalents of oxidizing agent such as pyridium chlorochromate and managese dioxide in a solvent such as methylene chloride and chloroform at an appropriate temperature of −78° C. to the boiling point of the solvent used.

The intermediate and desired product can be isolated and purified by a purification method generally used in organic synthetic chemistry, for example, filtration, extraction, washing, drying, concentration, recrystallization, various chromatography process, or the like. The intermediate may be used in the subsequent reaction without purification.

In the case where a salt of compound (I) is desired, and it is obtained in the form of the desired salt, it may be subjected to purification as such. In the case where compound (I) is obtained in a free form and its salt is desired, it may be dissolved or suspended in an appropriate solvent, and an acid or a base may be added thereto to form a salt.

Compound (I) or pharmaceutically acceptable salts thereof may be in the form of an adduct with water or various solvents, which are also within the scope of the present invention.

Compounds (I) obtained by the above production processes include all possible steroisomers and mixtures thereof. Table 1 shows examples of compounds (I) obtained by the above-described production processes.

TABLE 1

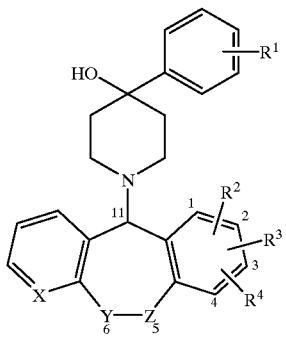

| Compound | X | Y—Z | $R^1$ | $R^2, R^3, R^4$ |
|---|---|---|---|---|
| 1 | CH | $CH_2$—O | H | H |
| 2 | CH | $CH_2$—O | H | 2-$CH_3$ |
| 3 | CH | $CH_2$—O | 3-$CH_3$ | 2-$CH_3$ |
| 4 | CH | $CH_2$—O | 3-$CF_3$ | 2-$CH_3$ |
| 5 | CH | $CH_2$—O | 4-Cl | 2-$CH_3$ |
| 6 | CH | $CH_2$—O | 2-$OCH_3$ | 2-$CH_3$ |
| 7 | CH | $CH_2$—O | 3-$OCH_3$ | 2-$CH_3$ |
| 8 | CH | $CH_2$—O | H | 2-$CH_2CH_3$ |
| 9 | CH | $CH_2$—O | H | 2-Br |
| 10 | CH | $CH_2$—O | H | 3-Br |
| 11 | CH | $CH_2$—O | H | 2-$NO_2$ |
| 12 | CH | $CH_2$—O | H | 2-$SCH_3$ |
| 13 | CH | $CH_2$—O | H | 2-$OCH_3$ |
| 14 | CH | $CH_2$—O | H | 2-$CO_2CH_3$ |
| 15 | CH | $CH_2$—O | H | 2-$CO_2H$ |
| 16 | CH | $CH_2$—O | H | 2-$CH_2CO_2CH_3$ |
| 17 | CH | $CH_2$—O | H | 2-$CH_2CO_2H$ |
| 18 | CH | $CH_2$—O | H | 2-$COCH_3$ |
| 19 | CH | $CH_2$—O | H | 2-$CH_2OH$ |
| 20 | CH | $CH_2$—O | H | 2-CHO |
| 21 | CH | $CH_2$—O | H | 2-$CH_2CH_2OH$ |
| 22 | CH | $CH_2$—O | H | 2-$CH(OH)CH_3$ |
| 23 | CH | $CH_2$—O | 3-$CF_3$ | 2-$CO_2CH_3$ |
| 24 | CH | $CH_2$—O | 3-$CF_3$ | 2-$CH_2OH$ |
| 25 | CH | $CH_2$—O | H | 2-$CH_3$, 4-$CO_2CH_3$ |
| 26 | N | $CH_2$—O | H | H |
| 27 | N | $CH_2$—O | H | 2-$CH_3$ |
| 28 | CH | $CH_2$—$CH_2$ | H | H |
| 29 | CH | CH=CH | H | H |
| 30 | CH | CONH | H | H |
| 31 | CH | $CH_2$—O | H | 2-$OCH_2OCH_3$ |
| 32 | CH | $CH_2$—O | H | 2-OH |
| 33 | CH | $CH_2$—O | 4-Br | 2-$CH_3$ |

The pharmacological activities of compounds (1) are described below.

Test Example 1

Evaluation Test of Analgesic Activity

Test compounds (10 mg/kg) were orally administered to groups of male mice, each group consisting of 4 to 12 mice, and after 1 hour, the mice were administered intraperitoneally with a 0.7% acetic acid aqueous solution in a dose of 0.1 ml per weight of 10 g. Then, the number of the risings manifested for 5 minutes 10 minutes after the administration was compared with a control group to calculate inhibition rate. Table 2 shows the results of typical compounds.

TABLE 2

| Compound | Inhibition Rate (%) |
|---|---|
| 2 | 83 |
| 3 | 90 |
| 4 | 96 |
| 5 | 72 |
| 8 | 94 |
| 19 | 76 |
| 22 | 100 |
| 24 | 100 |
| 27 | 100 |

Test Example 2

Acute Toxicity Test

Test compounds were intraperitoneally administered to groups of ddy male mice weighing 20±1 g. Seven days after the administration, the mortality was observed to determine minimum lethal dose (MLD) of each compound. Table 3 shows the results of typical compounds.

TABLE 3

| Compound | MLD (mg/kg) |
|---|---|
| 2 | >100 |
| 3 | >100 |
| 4 | >100 |
| 5 | >100 |
| 8 | >100 |
| 19 | >100 |
| 22 | >100 |
| 24 | >100 |

Compounds (I) or pharmaceutically acceptable salts thereof can be administered singly; however, they are preferably provided as various types of medical formulations. These medical formulations are used for animals and humans.

As the administration route, a route most effective for treatment is preferably used, for example, an oral route or a perenteral route such as an intrarectal route, an intraoral route, a subcutaneous route, an intramuscular route and an intraveous route is mentioned.

As the administration form, a capsule, a tablet, granules, a powder, syrup, an emulsion, a suppository, an injection, and the like can be used.

Liquid formulations such as an emulsion and syrup suitable for oral administration can be produced by using water; a saccharide such as sucrose, sorbitol and fructose; glycol such as polyethylene glycol and propylene glycol; oil such as sesame oil, olive oil and soybean oil; an antiseptic such as p-hydroxybenzoate; and a flavor such as strawberry flavor and peppermint. A capsule, a tablet, a powder and granules can be produced by using an excipient such as lactose, glucose, sucrose and mannitol; a disintegrator such as starch and sodium alginate; a lubricant such as magnesium stearate and talc; a binder such as polyvinyl alcohol, hydroxypropyl cellulose and gelatin; a surfactant such as a fatty acid ester; and a placticizer such as glycerin.

Formulations suitable for parenteral administration are sterilized aqueous formulations preferably containing an active compound isotonic with the blood of an acceptor. For example, for an injection, an injection solution is prepared by using a carrier composed of a salt solution, a glucose solution or a mixture of salt water and a glucose solution.

A local formulation is prepared by dissolving or suspending an active compound in at least one medium such as mineral oil, petroleum, polyhydric alcohol, or another base used for local medical formulations.

Formulations for intestinal administration are provided as suppositories prepared by using ordinary carriers such as cacao butter, hydrogenated fat and hydrogenated carboxylic acids.

Also at least one auxiliary component selected from a diluent, a flavor, an antiseptic (including an antioxidant), an excipient, a disintegrator, a lubricant, a binder, a surfactant, a pasticizer, etc., which are described above for the oral formulations, can be added to the above parenteral formulations.

The effective dose and the administration schedule of compounds (I) or pharmaceutically acceptable salts thereof vary depending upon the administration form, the age and weight of a patient, and the properties and graveness of symptoms to be treated. However, it is generally preferred to administer compound (I) or its pharmaceutically acceptable salts in a dose of 0.1 to 1000 mg/patient per day in once or several times a day.

EXAMPLES

Example 1

11-(4-Hydroxy-4-phenylpiperidine-1-yl)-6,11-dihydrodibenzo[b,e] oxepine (Compound 1)

To an ice-cooled suspension of 6,11-dihydrodibenzo[b,e] oxepine-11-ol (4.0 g) in methylene chloride (80 ml) was added thionyl chloride (2.74 ml). The mixture was stirred at room temperature for 1 hour. The reaction mixture was then concentrated under reduced pressure to give 11-chloro-6,11-dihydrodibenzo[b,e] oxepine as an oily substance. The whole substance was used for next reaction without isolation and purification.

To an ice-cooled solution of 4-hydroxy-4-phenylpiperidine (5.0 g) in methylene chloride (30 ml) were added triethylamine (5 ml) and the solution of 11-chloro-6,11-dihydrodibenzo[b,e] oxepine in methylene chloride (20 ml), and the mixture was stirred at room temperature for one night. To the reaction mixture was added water, and the mixture was subjected to extraction with chloroform. The organic layer was washed with a saturated aqueous solution of sodium chloride, dried over magnesium sulfate, and concentrated under reduced pressure. The residue was purified by silica gel column chromatography (hexane:ethyl acetate=10:1) to give compound 1 (3.92 g) as white crystals.

Melting point: 163–165° C.

Elementary analysis (%) for $C_{25}H_{25}NO_2$

|  | C | H | N |
|---|---|---|---|
| Calculated; | 80.83 | 6.78 | 3.77 |
| Found; | 80.75 | 7.04 | 3.70 |

IR (KBr) cm$^{-1}$: 3400, 2960, 2805, 1600, 1565, 1480, 1320, 1250, 1225, 1000.

$^1$H-NMR (CDCl$_3$) (δ, ppm): 1.60–1.80 (m, 2H), 1.91–2.17 (m, 2H), 2.35–2.50 (m, 2H), 2.57–2.68 (m, 1H), 2.76–2.87 (m, 1H), 3.99 (s, 1H), 4.73 (d, 1H, J=11.2 Hz), 6.75–6.85 (m, 2H), 6.94 (d, 1H, J=11.2 Hz), 7.12–7.39 (m, 9H), 7.43–7.50 (m, 2H).

Example 2

11-(4-Hydroxy-4-phenylpiperidine-1-yl)-2-methyl-6,11-dihydrodibenzo[b,e] oxepine (Compound 2)

Compound 2 (Step A)

Compound 2 (5.47 g) was obtained as a colorless syrupy substance by the same process as Example 1 except that 2-methyl-6,11-dihydrodibenzo[b,e] oxepine-11-ol (4.0 g) and 4-hydroxy-4-phenylpiperidine (3.8 g) were used.

IR(CHCl$_3$) cm$^{-1}$: 3400, 1647, 1507, 1368, 1247, 1219, 1183, 986, 928.

$^1$H-NMR(CDCl$_3$) (δ, ppm): 1.64–1.79 (m, 2H), 1.93–2.13 (m, 2H), 2.24 (s, 3H), 2.36–2.46 (m, 2H), 2.60–2.64 (m, 1H), 2.80–2.84 (m, 1H), 3.94 (s, 1H), 4.71 (d, 1H, J=11.6 Hz), 6.69–6.72 (m, 1H), 6.89 (d, 1H, J=11.6 Hz), 6.96–6.99 (m, 2H), 7.20–7.37 (m, 7H), 7.46–7.49 (m, 2H).

Fumarate of compound 2 (Step B)

To an ice-cooled solution of compound 2 (4.17 g) in isopropanol (80 ml) was added fumaric acid (1.26 g), and the mixture was stirred at room temperature for 8 hours. The resulting crystals were collected by filtration, and dried under reduced pressure to give fumarate hydrate (4.14 g) of compound 2 as white crystals.

Melting point: 180.5–181.5° C.

Elementary analysis (%) for $C_{26}H_{27}NO_2.H_2O.C_4H_4O_4$

|  | C | H | N |
|---|---|---|---|
| Calculated; | 69.35 | 6.40 | 2.70 |
| Found; | 69.37 | 6.71 | 2.42 |

Example 3

11-[4-Hydroxy-4-(3-methylphenyl)piperidine-1-yl]-2-methyl- 6,11-dihydrodibenzo[b,e] oxepine (Compound 3)

Compound 3

Compound 3 (0.95 g) was obtained as an amorphous substance by the same process as Example 1 except that 2-methyl-6,11-dihydrodibenzo[b,e] oxepine-1-ol (0.9 g) and 4-hydroxy-4-(3-methylphenyl)piperidine (0.92 g) were used.

IR(CHCl$_3$) cm$^{-1}$: 3500, 2910, 1500, 1260, 1220, 1200, 1120, 1045, 1010.

$^1$H-NMR (CDCl$_3$) (δ, ppm): 1.62–1.76 (m, 2H), 1.92–2.16 (m, 2H), 2.40–2.46 (m, 2H), 2.59–2.63 (m, 1H), 2.79–2.83 (m, 1H), 3.94 (s, 1H), 4.71 (d, 1H, J=11.4 Hz), 6.69–6.72 (m, 1H), 6.90 (d, 1H, J=11.4 Hz), 6.95–6.98 (m, 1H), 7.05–7.07 (m, 1H), 7.20–7.35 (m, 8H).

Fumarate of Compound 3

0.5 fumarate·0.2 hydrate (1.09 g) of compound 3 was obtained as white crystals by the same process as Step B of Example 2 except that compound 3 (0.95 g) and fumaric acid (0.28 g) were used.

Melting point: 197.5–198° C.

Elementary analysis (%) for $C_{27}H_{29}NO_2.0.2H_2O.0.5C_4H_4O_4$

|              | C     | H    | N    |
|--------------|-------|------|------|
| Calculated;  | 71.71 | 6.48 | 2.70 |
| Found;       | 71.77 | 6.59 | 2.67 |

Example 4

11-[4-Hydroxy-4-(3-trifluoromethylphenyl) piperidine-1-yl]-2-methyl-6,11-dihydrodibenzo[b,e] oxepine (Compound 4)

Compound 4

Compound 4 (3.54 g) was obtained as an amorphous substance by the same process as Example 1 except that 2-methyl-6,11-dihydrodibenzo[b,e] oxepine-1-ol (3.28 g) and 4-hydroxy-4-(3-trifluoromethylphenyl)piperidine (4.27 g) were used.

IR(CHCl$_3$) cm$^{-1}$: 3642, 1812, 1498, 1333, 1169, 1133, 1095, 990.

$^1$H-NMR (CDCl$_3$) (δ, ppm): 1.64–1.79 (m, 2H, 1.94–2.08 (m, 2H), 2.24 (s, 3H), 2.35–2.44 (m, 2H), 2.63–2.67 (m, 1H), 2.84–2.86 (m, 1H), 3.95 (s, 1H), 4.72 (d, 1H, J=11.5 Hz), 6.72 (d, 1H, J=8.3 Hz), 6.86 (d, 1H, J=11.5 Hz), 6.96–7.00 (m, 2H), 7.23–7.31 (m, 4H), 7.41–7.52 (m, 2H), 7.65 (d, 1H, J=7.6 Hz), 7.75 (s, 1H).

Sulfate of Compound 4

Sulfate (3.86 g) of compound 4 was obtained as white crystals by the same process as Step B of Example 2 except that compound 4 (3.44 g) and conc. sulfuric acid (0.32 ml) were used.

Melting point: 187.5–188° C.

Elementary analysis (%) for C$_{27}$H$_{26}$F$_3$NO$_2$.H$_2$SO$_4$

|              | C     | H    | N    |
|--------------|-------|------|------|
| Calculated;  | 58.79 | 5.12 | 2.54 |
| Found;       | 58.91 | 5.18 | 2.67 |

Example 5

11-[4-(4-Chlorophenyl)-4-hydroxypiperidine-1-yl]-2-methyl-6,11-dihydrodibenzo[b,e] oxepine (Compound 5)

Compound 5

Compound 5 (3.01 g) was obtained as a colorless syrupy substance by the same process as Example 1 except that 2-methyl-6,11-dihydrodibenzo[b,e] oxepine-11-ol (1.50 g) and 4-(4-chlorophenyl)-4-hydroxypiperidine (1.68 g) were used.

IR(CHCl$_3$) cm$^{-1}$: 3375, 1643, 1507, 1368, 1253, 1220, 1183, 1030, 984.

$^1$H-NMR(CDCl$_3$) (δ, ppm): 1.57–1.74 (m, 2H), 1.88–2.09 (m, 2H), 2.24 (s, 3H), 2.33–2.43 (m, 2H), 2.59–2.64 (m, 1H), 2.80–2.84 (m, 1H), 3.93 (s, 1H), 4.70 (d, 1H, J=11.6 Hz), 6.71 (d, 1H, J=7.9 Hz), 6.86 (d, 1H, J=11.6 Hz), 6.95–6.99 (m, 2H), 7.21– 7.31 (m, 6H), 7.36–7.43 (m, 2H).

Fumarate of Compound 5

Fumarate (1.6 g) of compound 5 was obtained as white crystals by the same process as Step B of Example 2 except that compound 5 (2.0 g) and fumaric acid (0.55 g) were used.

Melting point: 188–190° C.

Elementary analysis (%) for C$_{26}$H$_{26}$ClNO$_2$.C$_4$H$_4$O$_4$

|              | C     | H    | N    |
|--------------|-------|------|------|
| Calculated;  | 67.22 | 5.64 | 2.61 |
| Found;       | 67.06 | 5.68 | 2.65 |

Example 6

11-[4-Hydroxy-4-(2-methoxyphenyl)piperidine-1-yl]-2-methyl-6,11-dihydrodibenzo[b,e] oxepine (Compound 6)

Compound 6 (1.84 g) was obtained as white crystals by the same process as Example 1 except that 2-methyl-6,11-dihydrodibenzo[b,e]oxepine-11-ol (3.38 g) and 4-hydroxy-4-(2-methoxyphenyl)piperidine (3.5 g) were used.

Melting point: 200–201° C.

Elementary analysis (%) for C$_{27}$H$_{29}$NO$_3$.0.2(CH$_3$)$_2$CHOH

|              | C     | H    | N    |
|--------------|-------|------|------|
| Calculated;  | 77.69 | 7.35 | 3.21 |
| Found;       | 77.70 | 7.43 | 3.31 |

IR(KBr) cm$^{-1}$: 3550, 2950, 2920, 1595, 1580, 1495, 1460, 1225, 1125, 1015.

$^1$H-NMR (CDCl$_3$) (δ, ppm): 1.90–2.06 (m, 4H), 2.24 (s, 3H), 2.44–2.62 (m, 3H), 2.71–2.78 (m, 1H), 3.87 (s, 3H), 3.95 (s, 1H), 4.67 (d, 1H, J=11.5 Hz), 6.67–6.73 (m, 1H), 6.87–6.97 (m, 5H), 7.18–7.30 (m, 6H).

Example 7

11-[4-Hydroxy-4-(3-methoxyphenyl)piperidine-1-yl]-2-methyl-6,11-dihydrodibenzo[b,e] oxepine (Compound 7)

Compound 7 (1.69 g) was obtained by the same process as Example 1 except that 2-methyl-6,11-dihydrodibenzo[b, e] oxepine-11-ol (1.64 g) and 4-hydroxy-4-(3-methoxyphenyl)piperidine (1.5 g) were used.

Melting point: 157–158° C.

Elementary analysis (%) for C$_{27}$H$_{29}$NO$_3$.0.2H$_2$O

|              | C     | H    | N    |
|--------------|-------|------|------|
| Calculated;  | 77.37 | 7.03 | 3.34 |
| Found;       | 77.39 | 7.14 | 3.34 |

IR(KBr) cm$^{-1}$: 3490, 2945, 2915, 2810, 1600, 1500, 1260, 1220, 1015.

$^1$H-NMR (CDCl$_3$) (δ, ppm): 1.61–1.77 (m, 2H), 1.91–2.12 (m, 2H), 2.24 (s, 3H, 2.35–2.45 (br, 2H), 2.59–2.63 (m, 1H), 2.79–2.85 (m, 1H), 3.80 (s 3H), 3.94 (s, 1H), 4.71 (d, 1H, J=11.5 Hz), 6.69–6.73 (m, 1H), 6.76–6.81 (m, 1H), 6.89 (d, 1H, J=11.5 Hz), 6.96–7.06 (m, 4H), 7.21–7.35 (m, 5H).

Example 8

2-Ethyl-11-(4-hydroxy-4-phenylpiperidine-1-yl)-6,11-dihydrodibenzo[b,e] oxepine (Compound 8)

Compound 8

Compound 8 (5.12 g) was obtained as an amorphous substance by the same process as Example 1 except that 2-ethyl-6,11-dihydrodibenzo[b,e] oxepine-11-ol (3.67 g) and 4-hydroxy-4-phenylpiperidine (3.55 g) were used.

IR(CHCl$_3$) cm$^{-1}$: 3450, 2960, 2810, 1605, 1495, 1445, 1255, 1225, 1120, 1010.

$^1$H-NMR (DMSO-d$_6$) ($\delta$, ppm): 1.14 (t, 3H, J=7.6 Hz), 1.51–1.61 (m, 2H), 1.72–1.93 (m, 2H), 2.42–2.62 (m, 6H), 4.06 (s, 1H), 4.76 (d, 1H, J=11.6 Hz), 6.63 (s, 2H), 6.67 (d, 1H, J=8.3 Hz), 6.77 (d, 1H, J=11.5 Hz), 6.99–7.05 (m, 2H), 7.15–7.20 (m, 2H), 7.25–7.40 (m, 6H), 7.44–7.47 (m, 2H).

Fumarate of Compound 8

Fumarate·0.5 hydrate (2.6 g) of compound 8 was obtained as white crystals by the same process as Step B of Example 2 except that compound 8 (3.0 g) and fumaric acid (0.87 g) were used.

Melting point: 159–160° C.

Elementary analysis (%) for C$_{27}$H$_{29}$NO$_2$·0.5H$_2$O·C$_4$H$_4$O$_4$

|  | C | H | N |
|---|---|---|---|
| Calculated; | 70.97 | 6.53 | 2.72 |
| Found; | 70.70 | 6.79 | 2.67 |

Example 9

2-Bromo-11-[4-hydroxy-4-phenylpiperidine-1-yl]-6,11-dihydrodibenzo[b,e]oxepine (Compound 9)

Compound 9 (1.39 g) was obtained as an amorphous substance by the same process as Example 1 except that 2-bromo-6,11-dihydrodibenzo[b,e] oxepine-11-ol (1.5 g) and 4-hydroxy-4-phenylpiperidine (1.1 g) were used.

IR(CHCl$_3$) cm$^{-1}$: 3400, 2948, 2800, 1590, 1405, 1254, 1227, 1202, 1120, 1010.

$^1$H-NMR (CDCl$_3$) ($\delta$, ppm): 1.66–1.80 (m, 2H), 1.92–2.17 (m, 2H), 2.39–2.48 (m, 2H), 2.53–2.61 (m, 1H), 3.92 (s, 1H), 4.73 (d, 1H), J=11.5 Hz), 6.69 (d, 1H, J=8.9Hz), 6.89 (d, 1H, J=11.5 Hz), 7.22–7.39 (m, 9H), 7.46 (m, 2H).

Example 10

3-Bromo-11-(4-hydroxy-4-phenylpiperidine-1-yl)-6,11-dihydrodibenzo[b,e] oxepine (Compound 10)

Compound 10

Compound 10 (1.3 g) was obtained as an amorphous substance by the same process as Example 1 except that 3-bromo-6,11-dihydrodibenzo[b,e] oxepine-11-ol (1.5 g) and 4-hydroxy-4-phenylpiperidine (1.0 g) were used.

IR(CHCl$_3$) cm$^{-1}$: 3500, 2948, 2810, 1720, 1590, 1480, 1405, 1290, 1220, 1010.

$^1$H-NMR (CDCl$_3$) ($\delta$, ppm): 1.65–1.78 (m, 2H), 1.92–2.17 (m, 2H), 2.35–2.46 (m, 2H), 2.58–2.62 (m, 1H), 2.77–2.81 (m, 1H), 3.95 (s, 1H), 4.73 (d, 1H, J=11.5 Hz), 6.89–7.03 (m, 3H), 7.22–7.37 (m, 7H), 7.44–7.49 (m, 2H).

Oxalate of Compound 10

Oxalate·0.6 hydrate (1.3 g) of compound 10 was obtained as white crystals by the same process as Step B of Example 2 except that compound 10 (1.3 g) and oxalic acid (0.3 g) were used.

Melting point: 111.5–115° C.

Elementary analysis (%) for C$_{25}$H$_{24}$BrNO$_2$·0.6H$_2$O·C$_2$H$_2$O$_4$

|  | C | H | N |
|---|---|---|---|
| Calculated; | 58.83 | 4.97 | 2.54 |
| Found; | 58.57 | 4.90 | 2.29 |

Example 11

11-(4-Hydroxy-4-phenylpiperidine-1-yl)-2-nitro-6,11-dihydrodibenzo[b,e] oxepine (Compound 11)

Compound 11 (2.33 g) was obtained as pale yellow crystals by the same process as Example 1 except that 2-nitro-6,11-dihydrodibenzo[b,e] oxepine-11-ol (1.87 g) and 4-hydroxy-4-phenylpiperidine (2.01 g) were used.

Melting point: 111.5–114° C.

Elementary analysis (%) for C$_{25}$H$_{24}$N$_2$O$_4$·(CH$_3$)$_2$CHOH

|  | C | H | N |
|---|---|---|---|
| Calculated; | 70.57 | 6.77 | 5.88 |
| Found; | 70.52 | 7.12 | 5.95 |

IR(KBr) cm$^{-1}$: 3450, 2948, 2816, 1615, 1509, 1485, 1339, 1255, 1097, 993.

$^1$H-NMR(CDCl$_3$) ($\delta$, ppm): 1.67–1.80 (m, 2H), 1.93–2.16 (m, 2H), 2.43–2.70 (m, 2H), 2.74–2.78 (m, 1H), 4.09 (s, 1H), 4.85 (d, 1H, J=11.6 Hz), 6.87 (d, 1H, J=9.2 Hz), 7.05 (d, 1H, J=11.6 Hz), 7.18–7.49 (m, 9H), 8.03 (dd, 1H, J=2.8, 9.1 Hz), 8.15 (d, 1H, J=2.6 Hz).

EXAMPLE 12

11-(4-Hydroxy-4-phenylpiperidine-1-yl)-2-methylthio-6,11-dihydrodibenzo[b,e] oxepine (Compound 12)

Compound 12

Compound 12 (2.24 g) was obtained as white crystals by the same process as Example 1 except that 2-methylthio-6,11-dihydrodibenzo[b,e] oxepine-11-ol (1.5 g) and 4-hydroxy-4-phenylpiperidine (1.3 g) were used.

IR(CHCl$_3$) cm$^{-1}$:3460, 2946, 2808, 1725, 1479, 1385, 1248, 1125, 1043, 1008.

$^1$H-NMR(CDCl$_3$) ($\delta$, ppm):1.65–1.80(m, 2H), 1.94–2.17 (m, 2H), 2.37–2.47(m, 5H), 2.59–2.63(m, 1H), 2.79–2.83 (m, 1H), 3.95(s, 1H), 4.72(d, 1H, J=11.5 Hz), 6.77(d, 1H, J=9.2 Hz), 6.90(d, 1H, J=11.5 Hz), 7.13–7.17(m, 1H), 7.22–7.37(m, 8H, 7.46–7.49(m, 2H).

Oxalate of compound 12

Oxalate·0.5 hydrate (2.3 g) of compound 12 was obtained as white crystals by the same process as Step B of Example 2 except that compound 12 (2.24 g) and oxalic acid (0.53 g) were used.

Melting point: 120–120.5° C.

Elementary analysis (%) for C$_{26}$H$_{27}$NO$_2$S·0.5H$_2$O·C$_2$H$_2$O$_4$

|  | C | H | N |
|---|---|---|---|
| Calculated; | 65.10 | 5.85 | 2.71 |
| Found; | 64.77 | 5.88 | 2.51 |

EXAMPLE 13

11-(4-Hydroxy-4-phenylpiperidine-1-yl)-2-methoxy-6,11-dihydrodibenzo[b,e] oxepine (Compound 13)

Compound 13

Compound 13 (4.84 g) was obtained as an amorphous substance by the same process as Example 1 except that 2-methoxy-6,11-dihydrodibenzo[b,e] oxepine-11-ol (3.93 g) and 4-hydroxy-4-phenylpiperidine (1.14 g) were used.

IR(CHCl$_3$) cm$^{-1}$:3405, 2950, 2830, 1495, 1465, 1260, 1220, 1150, 1045, 760.

$^1$H-NMR(CDCl$_3$) (δ, ppm):1.64–1.77(m, 2H), 1.95–2.14 (m, 2H), 2.38–2.47(m, 2H), 2.59–2.63(m, 1H), 2.81–2.86 (m, 1H), 3.75(s, 3H), 3.94(s, 1H), 4.71(d, 1H, J=11.5 Hz), 6.70–6.76(m, 3H), 6.82(d, 1H, J=11.5 Hz), 7.21–7.49(m, 9H).

Fumarate of compound 13

Fumarate.isopropanol adduct (4.84 g) of compound 13 was obtained as white crystals by the same process as Step B of Example 2 except that compound 13 (3.93 g) and fumaric acid (1.14 g) were used.

Melting point: 161–163° C.

Elementary analysis (%) for $C_{26}H_{27}NO_3 \cdot (CH_3)_2CHOH \cdot C_4H_4O_4$

|  | C | H | N |
|---|---|---|---|
| Calculated; | 68.61 | 6.80 | 2.42 |
| Found; | 68.40 | 7.00 | 2.50 |

EXAMPLE 14

Methyl 11-(4-hydroxy-4-phenylpiperidine-1-yl)-6,11-dihydrodibenzo[b,e] oxepine-2-carboxylate (Compound 14)

Compound 14 (3.12 g) was obtained as a colorless syrupy substance by the same process as Example 1 except that methyl 11-hydroxy-6,11-dihydrodibenzo[b,e] oxepine-2-carboxylate (2.5 g) and 4-hydroxy-4-phenylpiperidine (1.91 g) were used.

IR (CHCl$_3$) cm$^{-1}$:2956, 1716, 1614, 1496, 1461, 1439, 1293, 1253, 1123, 1004. $^1$H-NMR(CDCl$_3$) (δ, ppm) :1.61–1.72(m, 2H), 1.86–2.08(m, 2H), 2.35–2.47(m, 2H), 2.54–2.62(m, 1H), 2.70–2.74(m, 1H), 3.82(s, 3H), 4.02(s, 1H), 4.74(d, 1H, J=11.6 Hz), 6.78(d, 1H, J=8.6 Hz), 6.96(d, 1H, J=11.6 Hz), 7.16–7.32(m, 7H), 7.40–7.44(m, 2H), 7.77 (dd, 1H, J=2.3, 8.6 Hz), 7.86(d, 1H, J=2.3 Hz).

EXAMPLE 15

11-(4-Hydroxy-4-phenylpiperidine-1-yl)-6,11-dihydrodibenzo[b,e] oxepine-2-carboxylic acid (Compound 15)

To a solution of compound 14 (1.75 g) obtained in Example 14 in ethanol (35 ml) was added 10N aqueous sodium hydroxide (1.23 ml), and the mixture was stirred at 60° C. for two and a half hours. The reaction mixture was concentrated under reduced pressure, water was added to the residue, and the mixture was adjusted to pH 4 with 4N aqueous hydrochloric acid. The resulting solid was collected by filtration and dried under reduced pressure to give compound 15 (0.9 g) as white crystals.

Melting point: 151–154° C.

Elementary analysis (%) for $C_{26}H_{25}NO_4 \cdot 0.8H_2O$

|  | C | H | N |
|---|---|---|---|
| Calculated; | 72.64 | 6.24 | 3.26 |
| Found; | 72.49 | 5.90 | 2.89 |

IR(KBR) cm$^{-1}$:3400, 1704, 1694, 1612, 1508, 1380, 1233, 1120, 1010. $^1$H-NMR(CDCl$_3$) (δ, ppm):193–1.97(m, 2H), 2.48–2.58(m, 6H), 4.25(s, 1H), 4.88(s, 1H), 4.96(d, 1H, J=11.4 Hz), 6.89(d, 1H. J=8.3 Hz), 6.96(d, 1H, J=11.4 Hz), 7.21–7.53(m, 9H), 7.79(dd, 1H, J=2.1, 8.4 Hz), 7.92(s, 1H), 12.72(br, 1H).

EXAMPLE 16

Methyl 11-(4-hydroxy-4-phenylpiperidine-1-yl)-6,11-dihydrodibenzo[b,e] oxepine-2-acetate (Compound 16)

Compound 16

Compound 16 (2.97 g) was obtained as a colorless syrupy substance by the same process as Example 1 except that methyl 11-hydroxy-6,11-dihydrodibenzo[b,e] oxepine-2-acetate (2.5 g) and 4-hydroxy-4-phenylpiperidine (3.02 g) were used.

IR (CHCl$_3$) cm$^{-1}$:2952, 2814, 1735, 1496, 1316, 1259, 1152, 1123, 1092, 1007. $^1$H-NMR(CDCl$_3$) (δ, ppm) :1.70–1.79(m, 2H), 1.93–2.17(m, 2H), 2.38–2.46(m, 2H), 2.60–2.64(m, 1H), 2.79–2.84(m, 1H), 3.52(s, 2H), 3.67(s, 3H), 3.98(s, 1H), 4.72(d, 1H, J=11.4 Hz), 6.78(dd, 1H, J=1.0, 7.6 Hz), 6.91(d, 1H, J=11.4 Hz), 7.07–7.11(m, 2H), 7.22–7.37(m, 7H), 7.47–7.50(m, 2H).

Fumarate of compound 16

Fumarate.0.5 hydrate (0.9 g) of compound 16 was obtained as white crystals by the same process as step B of Example 2 except that compound 16 (1.2 g) and fumaric acid (0.31 g) were used.

Melting point: 168–171° C.

Elementary analysis (%) for $C_{28}H_{29}NO_4 \cdot 0.5H_2O \cdot C_4H_4O_4$

|  | C | H | N |
|---|---|---|---|
| Calculated; | 67.59 | 6.03 | 2.46 |
| Found; | 67.18 | 6.35 | 2.30 |

EXAMPLE 17

11-(4-Hydroxy-4-phenylpiperidine-1-yl)-6,11-dihydrodibenzo[b,e] oxepine-2-acetic acid (Compound 17)

Compound 17 (0.86 g) was obtained as white crystals by the same process as Example 15 except that compound 16 (1.33 g) obtained in Example 16 was used.

Melting point: 145–147° C.

Elementary analysis (%) for $C_{27}H_{27}NO_4 \cdot 0.5H_2O$

|  | C | H | N |
|---|---|---|---|
| Calculated; | 73.95 | 6.43 | 3.19 |
| Found; | 74.15 | 6.67 | 3.08 |

IR(KBr) cm$^{-1}$:3050, 3010, 2955, 2800, 1710, 1575, 1495, 1380, 1250, 1120, 1005.

$^1$H-NMR(CDCl$_3$) (δ, ppm):1.59–1.75(m, 2H), 1.90–2.11 (m, 2H), 2.35–2.50(m, 2H), 2.57–2.69(m, 1H), 2.75–2.86 (m, 1H), 3.55(s, 2H), 4.05(s, 1H), 4.72(d, 1H, J=11.9 Hz), 6.75–6.84(m, 2H), 7.08–7.14(m, 2H), 7.20–7.37(m, 7H), 7.42–7.49(m, 2H).

EXAMPLE 18

2-Acetyl-11-(4-hydroxy-4-phenylpiperidine-1yl)-6,11-dihydrodibenzo[b,e] oxepine (Compound 18)

Compound 18 (0.97 g) was obtained as white crystals by the same process as Example 1 except that 2-acetyl-11-hydroxy-6,11-dihydrodibenzo[b,e] oxepine (0.72 g) and 4-hydroxy-4-phenylpiperidine (0.6 g) were used.

Melting point: 165–167° C.

Elementary analysis (%) for $C_{27}H_{27}NO_3 \cdot 0.33(CH_3)_2CHOH$

|  | C | H | N |
|---|---|---|---|
| Calculated; | 77.57 | 6.90 | 3.23 |
| Found; | 77.63 | 7.07 | 3.33 |

IR(KBr) cm$^{-1}$:3440, 2950, 1665, 1600, 1495, 1360, 1305, 1250, 1240, 1130. $^1$H-NMR(CDCl$_3$) (δ, ppm);167–1.78(m, 2H), 1.93–2.14(m, 2H), 2.39–2.54(m, 2H), 2.59–2.67(m, 1H), 2.74–2.79(m, 1H), 4.09(s, 1H), 4.80(d, 1H, J=11.4 Hz), 6.85(d, 1H, J=8.6 Hz), 7.03(d, 1H, J=11.4 Hz), 7.19–7.37(m, 7H), 7.45–7.49(m, 2H), 7.77(dd, 1H, J=2.3, 8.6 Hz), 7.85(d, 1H, J=2.3 Hz).

EXAMPLE 19

11-(4-Hydroxy-4-phenylpiperidine-1-yl)-2-hydroxymethyl-6,11-dihydrodibenzo[b,e] oxepine (Compound 19)

To a suspension of lithium aluminum hydride (0.41 g) in tetrahydrofuran (THF) (20 ml) cooled to −5° C. was added a THF solution (150 ml) of compound 14 (1.54 g) obtained in Example 14 in a nitrogen atmosphere, and the mixture was stirred at the same temperature for 30 minutes. To the reaction mixture was added aqueous ammonia (0.5 ml), and the mixture was further stirred at room temperature for 2 hours. The reaction mixture was dried over magnesium sulfate, and concentrated under reduced pressure. The residue was purified by silica gel column chromatography (hexane:ethyl acetate=1:1) to give compound 19 (0.5 g) as white crystals.

Melting point: 118–122° C.

Elementary analysis (%) for $C_{26}H_{27}NO_3 \cdot 0.5H_2O$

|  | C | H | N |
|---|---|---|---|
| Calculated; | 76.07 | 6.87 | 3.41 |
| Found; | 76.09 | 6.99 | 3.15 |

IR (KBr) cm$^{-1}$:3310, 2955, 2815, 1615, 1570, 1495, 1315, 1260, 1120, 1015. $^1$H-NMR(CDCl$_3$) (δ, ppm) :1.63–1.79(m, 2H), 1.92–2.16(m, 2H), 2.36–2.50(m, 2H), 2.57–2.68(m, 1H), 2.76–2.87(m, 1H), 4.02(s, 1H), 4.58(d, 2H, J=5.6 Hz), 4.74(d, 1H, J=11.6 Hz), 6.81(d, 1H, J=8.9 Hz), 6.94(d, 1H, J=11.6 Hz), 7.13–7.21(m, 2H), 7.21–7.41 (m, 7H), 7.45–7.51(m, 2H).

EXAMPLE 20

[11-(4-Hydroxy-4-phenylpiperidine-1-yl)-6,11-dihydrodibenzo[b,e] oxepine-2-yl]carbaldehyde (Compound 20)

To a solution of compound 19 (2.3 g) obtained in Example 19 in dichloromethane (80 ml) was added manganese dioxide (5.22 g), and the mixture was stirred at room temperature for 2 hours. A solid was removed by filtration from the reaction mixture, and the filtrate was concentrated under reduced pressure. The residue was purified by silica gel column chromatography (hexane:ethyl acetate=10:1) to give compound 20 (1.3 g) as white crystals.

Melting point: 166–168° C.

Elementary analysis (%) for $C_{26}H_{25}NO_3$

|  | C | H | N |
|---|---|---|---|
| Calculated; | 78.17 | 6.31 | 3.51 |
| Found; | 78.02 | 6.31 | 3.43 |

IR(KBr) cm$^{-1}$:3400, 2950, 2825, 1675, 1600, 1495, 1390, 1260, 1195, 1120. $^1$H-NMR (CDCl$_3$) (δ, ppm):168–1.79(m, 2H), 1.93–2.16(m, 2H), 2.43–2.56(m, 2H), 2.56–2.70(m, 1H), 2.71–2.84(m, 1H), 4.10(s, 1H), 4.83(d, 1H, J=11.4 Hz), 6.92(d, 1H, J=8.2 Hz), 7.05(d, 1H, J=11.4 Hz), 7.25–7.39(m, 7H), 7.46–7.49(m, 2H), 7.64–7.73(m, 2H), 9.84(s, 1H).

EXAMPLE 21

11-(4-Hydroxy-4-phenylpiperidine-1-yl)-2-(2-hydroxyethyl)-6,11-dihydrodibenzo[b,e] oxepine (Compound 21)

Compound 21 (0.92 g) was obtained as white crystals by the same process as Example 19 except that compound 16 (1.1 g) obtained in Example 16 was used.

Melting point: 104–107° C.

Elementary analysis (%) for $C_{27}H_{29}NO_3 \cdot 0.5H_2O$

|  | C | H | N |
|---|---|---|---|
| Calculated; | 76.39 | 7.12 | 3.30 |
| Found; | 76.67 | 7.51 | 3.05 |

IR(KBr) cm$^{-1}$:3320, 2950, 2800, 1615, 1500, 1260, 1220, 1120, 1040, 1010. $^1$H-NMR(CDCl$_3$) (δ, ppm):1.61–1.79(m, 2H), 1.90–2.11(m, 2H), 2.34–2.50(m, 2H), 257–2.70(m, 1H), 2.70–2.88(m, 3H), 3.72–3.87(m, 2H), 3.97(s, 1H), 4.72(d, 1H, J=11.6 Hz), 6.77(d, 1H, J=7.9 Hz), 6.90(d, 1H, J=11.6 Hz), 6.96–7.11(m, 2H), 7.14–7.45(m, 7H), 7.40–7.57 (m, 2H).

EXAMPLE 22

11-(4-Hydroxy-4Ophenylpiperidine-1-yl)-2-(1-hydroxyethyl)-6,11-dihydrodibenzo[b,e] oxepine (Compound 22)

Compound 22

A THF (50 ml) solution of compound 20 (2.3 g) obtained in Example 20 was cooled with ice in an argon atmosphere, and to the solution was added 1M methylmagnesium bromide-THF solution (12.4 ml), and the mixture was stirred at room temperature for 2 hours. To the reaction mixture was added aqueous ammonium chloride under ice cooling, and the mixture was subjected to extraction with ethyl acetate. The organic layer was washed with saturated brine, dried over magnesium sulfate, and concentrated under reduced pressure. The residue was purified by silica gel column chromatography (hexane:ethyl acetate=2:1) to give compound 22 (2.2 g) as an amorphous substance.

IR(CHCl$_3$) cm$^{-1}$:3330, 2955, 2815, 1610, 1495, 1315, 1255, 1225, 1120, 1010. $^1$H-NMR(CDCl$_3$) (δ, ppm):1.45–1.48(m, 3H), 1.65–1.81(m, 2H), 1.93–2.13(m, 2H, 2.38–2.47(br, 2H), 2.60–2.68(m, 1H), 2.76–2.86(m, 1H), 4.00(br, 1H), 4.73(d, 1H, J=11.6 Hz), 4.75–4.90(m, 1H), 6.79(d, 1H, J=8.9 Hz), 6.93(d, 1H, J=11.6 Hz), 7.15–7.38(m, 9H), 7.46–7.50(m, 2H).

Fumarate of compound 22

Fumarate (1.24 g) of compound 22 was obtained as white crystals by the same process as Step B of Example 2 except that compound 22 (1.51 g) and fumaric acid (0.42 g) were used.

Melting point: 169–171° C.

Elementary analysis (%) for C$_{27}$H$_{29}$NO$_3$.C$_4$H$_4$O$_4$

|  | C | H | N |
|---|---|---|---|
| Calculated; | 70.04 | 6.26 | 2.63 |
| Found; | 69.81 | 6.48 | 2.54 |

EXAMPLE 23

Methyl 11-[4-hydroxy-4-(3-trifluoromethylphenyl)piperidine-1-yl]-6,11-dihydrodibenzo[b,e] oxepine-2-carboxylate (Compound 23)

Compound 23 (3.12 g) was obtained as a colorless syrupy substance by the same process as Example 1 except that methyl 11-hydroxy-6,11-dihydrodibenzo[b,e] oxepine-2-carboxylate (2.5 g) and 4-hydroxy-4-(3-trifluorophenyl)piperidine (1.91 g) were used.

$^1$H-NMR(CDCl$_3$) (δ, ppm):1.62–1.80(m, 2H), 1.90–2.18 (m, 2H), 2.38–2.51(m, 2H), 2.61–2.70(m, 1H), 2.79–2.86 (m, 1H), 3.88(s, 3H), 4.09(s, 1H), 4.81(d, 1H, J=11.5 Hz), 6.84(d, 1H, J=8.6 Hz), 7.00(d, 1H, J=11.5 Hz), 7.13–7.35(m, 5H), 7.42–7.53(m, 1H), 7.63–7.68(m, 1H), 7.73–7.75(m, 1H), 7.83(dd, 1H, J=2.3, 8.6 Hz), 7.91(d, 1H, J=2.3 Hz).

EXAMPLE 24

11-[4-Hydroxy-4-(3-trifluoromethylphenyl)piperidine-1-yl]-2-hydroxymethyl-6,11-dihydrodibenzo[b,e] oxepine (Compound 24)

Compound 24

Compound 24 (2.04 g) was obtained as an amorphous substance by the same process as Example 19 except that compound 23 (3.2 g) obtained in Example 23 was used.

IR(CHCl$_3$) cm$^{-1}$:3350, 2950, 2815, 1610, 1450, 1330, 1260, 1160, 1125, 1010. $^1$H-NMR(CDCl$_3$) (δ, ppm):1.61–1.78(m, 2H), 1.92–2.15(m, 2H), 2.35–2.50(m, 2H), 2.60–2.70(m, 1H), 2.80–2.90(m, 1H), 3.94(s, 1H), 4.51–4.62(m, 2H), 4.75(d, 1H, J=11.5 Hz), 6.81(d, 1H, J=8.9 Hz), 6.91(d, 1H, J=11.5 Hz), 7.15–7.20(m, 2H), 7.21–7.31 (m, 4H), 7.41–7.54(m, 2H), 7.63–7.69(br, 1H), 7.75–7.90 (br, 1H).

Fumarate of compound 24

Fumarate (1.77 g) of compound 24 was obtained as white crystals by the same process as Step B of Example 2 except that compound 24 (1.83 g) and fumaric acid (0.45 g) were used.

Melting point: 178–180° C.

Elementary analysis (%) for C$_{27}$H$_{26}$F$_3$NO$_3$.C$_4$H$_4$O$_4$

|  | C | H | N |
|---|---|---|---|
| Calculated; | 63.58 | 5.16 | 2.39 |
| Found; | 63.57 | 5.21 | 2.38 |

EXAMPLE 25

Methyl 11-(4-hydroxy-4-phenylpiperidine-1-yl)-2-methyl-6,11-dihydrodibenzo[b,e] oxepine-4carboxylate (Compound 25)

Compound 25 (1.13 g) was obtained as white crystals by the same process as Example 1 except that methyl 11-hydroxy-2-methyl-6,11-dihydrodibenzo[b,e] oxepine-4-carboxylate (1.19 g) and 4-hydroxy-4-phenylpiperidine (0.98 g) were used.

Melting point: 133–135° C.

Elementary analysis (%) for C$_{29}$H$_{29}$NO$_4$.0.2H$_2$O

|  | C | H | N |
|---|---|---|---|
| Calculated; | 75.21 | 6.63 | 3.13 |
| Found; | 75.46 | 6.71 | 2.84 |

IR(KBr) cm$^{-1}$: 3465, 3010, 2950, 2830, 1715, 1580, 1475, 1300, 1215, 1140. $^1$H-NMR(CDCl$_3$) (δ, ppm):166–1.78(m, 2H), 1.93–2.10(m, 2H), 2.25(s, 3H), 2.36–2.44(br, 2H), 2.59–2.69(br, 1H), 2.79–2.82(br, 1H), 3.86(s, 3H), 3.99(s, 1H), 4.88(d, 1H, J=11.9 Hz), 5.86(d, 1H, J=11.9 Hz), 7.10(d, 1H, J=2.0 Hz), 7.22–7.37(m, 8H), 7.45–7.49(m, 2H).

EXAMPLE 26

5-(4-Hydroxy-4-phenylpiperidine-1-yl)-5,11-dihydrobenzo[3,4-b] oxepinopyridine (Compound 26)

Compound 26 (1.0 g) was obtained as white crystals by the same process as Example 1 except that 5,11-dihydrobenzo[3,4-b] oxepinopyridine-5-ol (1.5 g) and 4-hydroxy-4-phenylpiperidine (1.5 g) were used.

Melting point: 166.5–168° C.

Elementary analysis (%) for $C_{24}H_{24}N_2O_2$

|  | C | H | N |
|---|---|---|---|
| Calculated; | 77.39 | 6.49 | 7.52 |
| Found; | 77.21 | 6.79 | 7.33 |

IR(KBr) cm$^{-1}$:3650, 2800, 1570, 1490, 1220, 1110, 1050, 990. $^1$H-NMR(CDCl$_3$) (δ, ppm):1.63–1.78(m, 2H), 1.95–2.17(m, 2H), 2.40–2.50(m, 2H), 2.57–2.61(m, 1H), 2.77–2.81(m, 1H), 4.04(s, 1H), 5.00(d, 1H, J=12.0 Hz), 6.75(d, 1H, J=12.0 Hz), 6.85–6.94(m, 2H), 7.16–7.29(m, 4H), 7.32–7.38(m, 2H), 7.45–7.49(m, 2H), 7.59(dd, 1H, J=1.7, 7.6 Hz), 8.51(dd, 1H, J=1.7, 5.0 Hz).

EXAMPLE 27

5-(4-Hydroxy-4-phenylpiperidine-1-yl)-7-methyl-5,11-dihydrobenzo[3,4-b] oxepinopyridine (Compound 27)

Compound 27 (1.05 g) was obtained as white crystals by the same process as Example 1 except that 7-methyl-5,11-dihydrobenzo[3,4-b] oxepinopyridine-5-ol (2.05 g) and 4-hydroxy-4-phenylpiperidine (2.0 g) were used.

Melting point: 163–166° C.

Elementary analysis (%) for $C_{25}H_{26}N_2O_2$

|  | C | H | N |
|---|---|---|---|
| Calculated; | 77.69 | 6.78 | 7.25 |
| Found; | 77.43 | 6.84 | 7.19 |

IR(KBr) cm$^{-1}$: 3310, 2950, 2920, 2800, 1585, 1495, 1450, 1255, 1215, 1120. $^1$H-NMR(CDCl$_3$) (δ, ppm) :1.60–1.79(m, 2H), 1.94–2.13(m, 2H), 2.26(s, 3H), 2.36–2.50(m, 2H), 2.51–2.63(m, 1H), 2.75–2.83(m, 1H), 4.00(s, 1H), 4.96(d, 1H, J=12.4 Hz), 6.63(d, 1H, J=12.4 Hz), 6.82(d, 1H, J=8.3 Hz), 6.96–7.00(br, 1H), 7.01–7.06(br, 1H), 7.16–7.37(m, 4H), 7.45–7.52(m, 2H), 7.58(dd, 1H, J=1.3, 7.6 Hz), 8.50(dd, 1H, J=1.3 4.8 Hz).

EXAMPLE 28

5-(4-Hydroxy-4-phenylpiperidine-1-yl)-10,11-dihydro-5H-dibenzo[a,d] cycloheptene (Compound 28)

Compound 28 (1.48 g) was obtained as white crystals by the same process as Example 1 except that 10,11-dihydro-5H-dibenzo[a,d] cyclohepten-5-ol (1.2 g) and 4-hydroxy-4-phenylpiperidine (1.18 g) were used.

Melting point:155.5–156.5° C.

Elementary analysis (%) for $C_{26}H_{27}NO$

|  | C | H | N |
|---|---|---|---|
| Calculated; | 84.51 | 7.37 | 3.79 |
| Found; | 84.40 | 7.42 | 3.77 |

IR(KBr) cm$^{-1}$: 3400, 2918, 2804, 2342, 1517, 1493, 1129, 1087, 1048, 986. $^1$H-NMR(CDCl$_3$) (δ, ppm);1.66–1.73(m, 2H), 2.00–2.11(m, 2H), 2.30–2.64(m, 2H), 2.75–2.78(m, 2H), 2.80–2.86(m, 2H), 4.03–4.12(m, 3H), 7.04–7.31(m, 9H), 7.33–7.37(m, 2H), 7.47–7.51(m,2H).

EXAMPLE 29

5-(4-Hydroxy-4-phenylpiperidine-1-yl)-5H-dibenzo[a,d] cycloheptene (Compound 29)

Compound 29 (1.7 g) was obtained as white crystals by the same process as Example 1 except that 5H-dibenzo[a,d]cycloheptene-5-ol (1.0 g) and 4-hydroxy-4-phenylpiperidine (1.02 g) were used.

Melting point: 152–156° C.

Elementary analysis (%) for $C_{26}H_{25}NO.0.6H_2O$

|  | C | H | N |
|---|---|---|---|
| Calculated; | 82.55 | 6.98 | 3.70 |
| Found; | 82.51 | 7.06 | 3.97 |

IR(KBr) cm$^{-1}$: 3400, 2952, 2804, 1494, 1396, 1260, 1131, 1089, 1050, 986. $^1$H-NMR(CDCl$_3$) (δ, ppm):1.52–1.56(m, 2H), 1.73–1.85(m, 2H), 2.10–2.30(m, 4H), 4.42(s, 1H), 7.01(s, 2H), 7.18–7.43(m, 13H).

EXAMPLE 30

5,11-Dihydro-11-(4-hydroxy-40phenylpiperidine-1-yl)-6-oxo-11H-dibenzo[b,e] azepine (Compound 30)

Compound 30 (2.62 g) was obtained as white crystals by the same process as Example 1 except that 5,11-dihydro-5-oxo-11H-dibenzo[b,e] azepine-11-ol (2.0 g) and 4-hydroxy-4-phenylpiperidine (2.05 g) were used.

Melting point: 229–241° C.

Elementary analysis (%) for $C_{25}H_{24}N_2O_2.0.2H_2O$

|  | C | H | N |
|---|---|---|---|
| Calculated; | 77.37 | 6.33 | 7.22 |
| Found; | 77.39 | 6.54 | 7.16 |

IR(KBr) cm$^{-1}$: 3500, 3050, 2950, 2800, 1650, 1595, 1585, 1385, 1050, 760. $^1$H-NMR(CDCl$_3$) (δ, ppm):1.50–1.70(m, 2H), 1.91–2.09(m, 2H), 2.25–2.50(m, 4H), 4.21(s, 1H), 6.99(d, 1H, J=7.5 Hz), 7.09–7.16(m, 1H), 7.20–7.46(m, 10H), 7.91(dd, 1H, J=1.3, 7.5 Hz), 8.03(br, 1H).

EXAMPLE 31

11-(4-Hydroxy-4phenylpiperidine-1-yl)-2-methoxymethoxy-6,11-dihydrodibenzo[b,e] oxepine (Compound 31)

Compound 31 (1.4 g) was obtained as white crystals by the same process as Example 1 except that 2methoxymethoxy-6,11-dihydrodibenzo[b,e]oxepine-11-ol (1.11 g) and 4-hydroxy-4-phenylpiperidine (0.94 g) were used.

$^1$H-NMR(CDCl$_3$) (δ, ppm):1.61–1.81(m, 2H), 1.95–2.13 (m, 2H), 2.35–2.48(m, 2H), 2.56–2.65(m, 1H), 2.80–2.90 (m, 1H), 3.48(s, 3H), 3.94(s, 1H), 4.71(d, 1H, J=11.6 Hz), 5.09(s, 2H), 6.70–6.92(m, 4H), 7.21–7.38(m, 7H), 7.45–7.50(m, 2H).

EXAMPLE 32

2-Hydroxy-11-(4-hydroxy-4-phenylpiperidine-1yl)-6,11-dihydrodibenzo[b,e] oxepine (Compound 32)

To a solution of compound 31 (1.33 g) obtained in Example 31 in a mixture of tetrahydrofuran (25 ml) and isopropanol (15 ml) was added 4N aqueous hydrochloric acid (5 ml), and the mixture was stirred at room temperature for 3 hours. The reaction mixture was concentrated under reduced pressure, and water (20 ml) and dichloromethane (30 ml) were added to the residue for extraction. The organic layer was washed with saturated brine, dried over magnesium sulfate, and then concentrated under reduced pressure. The residue was purified by silica gel column chromatography (hexane:ethyl acetate=1:1) to give compound 32 (0.71 g) as white crystals.

Melting point: 141–144° C.

Elementary analysis (%) for $C_{25}H_{25}NO_3 \cdot 0.5(CH_3)_2CHOH$

|  | C | H | N |
|---|---|---|---|
| Calculated; | 76.23 | 7.00 | 3.35 |
| Found; | 76.40 | 6.89 | 3.32 |

IR(KBr) cm$^{-1}$:33450, 2960, 2840, 1710, 1590, 1500, 1280, 1210, 760, 700. $^1$H-NMR(CDCl$_3$) (δ, ppm);1.61–1.81(m, 2H), 1.91–2.15(m, 2H), 2.35–2.50(m, 2H), 2.51–2.65(m, 1H), 2.80–2.91(m, 1H), 3.90(s, 1H), 4.70(d, 1H, J=11.7 Hz), 6.61–6.72(m, 3H), 6.80(d, 1H, J=11.75 Hz), 7.21–7.38(m, 7H), 7.43–7.49(m, 2H).

EXAMPLE 33

11-[4-Hydroxy-4-(4-bromopheny)piperidine-1-yl]-2-metnyl-6,11-dihydrodibenzo[b,e] oxepine (Compound 33)

Compound 33 (1.56 g) was obtained as a colorless syrupy substance by the same process as Example 1 except that 11-hydroxy-2-methyl-6,11-dihydrodibenzo[b,e] oxepine (2.0 g) and 4-hydroxy-4-(4-bromophenyl)piperidine (2.3 g) were used.

IR(CHCl$_3$) cm$^{-1}$:2661, 1686, 1560, 1421, 1277, 1234, 1214, 1006. $^1$H-NMR(CDCl$_3$) (δ, ppm):1.48–1.60(m, 2H), 1.72–1.90(m, 2H), 2.26(s, 3H), 2.46–2.53(m, 3H), 2.57–2.60(m, 1H), 4.02(s, 1H), 4.13(d, 1H, J=11.4 Hz), 6.64(d, 1H, J=5.3 Hz), 6.76(d, 1H, J=11.4 Hz), 6.96–7.02(m, 2H), 7.30–7.48(m, 8H).

Fumarate of compound 33

Fumarate (1.76 g) of compound 33 was obtained as white crystals by the same process as Step B of Example 2 except that compound 33 (1.56 g) and fumaric acid (0.39 g) were used.

Melting point: 105–107° C.

Elementary analysis (%) for $C_{26}H_{26}BrNO_2 \cdot C_4H_4O_4 \cdot H_2O$

|  | C | H | N |
|---|---|---|---|
| Calculated; | 60.21 | 5.39 | 2.34 |
| Found; | 60.50 | 5.50 | 2.07 |

Formulation Example 1 Tablet

A tablet having the following composition was prepared in a conventional manner.

| Compound 2 | 100 mg |
|---|---|
| Lactose | 60 mg |

-continued

| Potato starch | 30 mg |
|---|---|
| Polyvinyl alcohol | 2 mg |
| Magnesium stearate | 1 mg |
| Tar dye | trace |

Formulation Example 2 Powder

A powder having the following composition is prepared in a conventional manner.

| Compound 1 | 150 mg |
|---|---|
| Lactose | 280 mg |

Formulation Example 3 Syrup

Syrup having the following composition is prepared in a conventional manner.

| Compound 2 | 100 mg |
|---|---|
| Refined saccharose | 40 g |
| Ethyl p-hydroxybenzoate | 40 mg |
| Propyl p-hydroxybenzoate | 10 mg |
| Strawberry flavor | 0.1 ml |

Water is added to a total amount of 100 cc.

Industrial Applicability

The present invention provides phenylpiperidine derivatives or pharmaceutically acceptable salts thereof useful as analgesics.

What is claimed is:

1. A phenylpiperidine derivative or pharmaceutical acceptable salt thereof represented by formula (I):

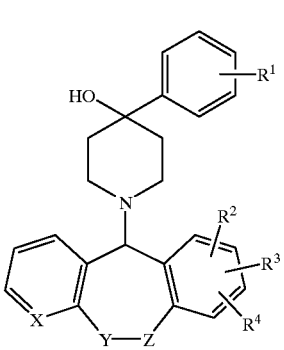

(I)

wherein X represents CH or N; Y-Z represents $Ch_2$—O, $CH_2$—S, $CH_2$—$CH_2$, CH=CH or CONR$^5$ (wherein R$^5$ represents hydrogen or lower alkyl); R$^1$ represents hydrogen, lower alkyl, halogen, lower alkoxy or trifluoromethyl; and R$^2$, R$^3$ and R$^4$ are the same or different and each represents hydrogen, lower alkyl or QR$^6$ (wherein Q represents a single bond or lower alkylene, and R$^6$ represents hydroxy, lower alkoxyalkoxy, lower alkoxy, lower alkylthio, nitro, halogen, lower alkanoyloxy, lower alkoxycarbonyl, lower alkanoyl or carboxyl).

2. The compound according to claim 1, wherein X is CH.

3. The compound according to claim 1, wherein X is N.

4. The compound according to claim 1, wherein Y-Z is $CH_2$—O.

5. The compound according to claim 1, wherein Y-Z is $CH_2$—$CH_2$.

6. The compound according to claim 1, wherein Y-Z is CH=CH.

7. The compound according to claim 1, wherein Y-Z is $CONR^5$ (wherein $R^5$ is defined as described above).

8. The compound according to claim 1, wherein Y-Z represents $CH_2$—O, $CH_2$—S, CH=CH or $CONR^5$.

9. The compound according to claim 1, wherein Y-Z represents $CH_2$—O, $CH_2$—S or $CONR^5$.

10. The compound according to claim 2, wherein Y-Z is $CH_2$—O.

11. The compound according to claim 2, wherein Y-Z is CH=CH.

12. The compound according to claim 2, wherein Y-Z is $CONR^5$.

13. The compound according to claim 2, wherein Y-Z represents $CH_2$—O, $CH_2$—S, CH=CH or $CONR^5$.

14. The compound according to claim 2, wherein Y-Z represents $CH_2$—O, $CH_2$—S or $CONR^5$.

15. The compound according to any one of claims 1, 2, 4–7 and 10–14, wherein $R^1$ is hydrogen or trifluoromethyl.

16. The compound according to any one of claims 1, 2, 4–7 and 8–14, wherein $R^2$, $R^3$ and $R^4$ independently represent hydrogen, lower alkyl or $QR^6$ (wherein Q represents lower alkylene and $R^6$ represents hydroxy).

17. A pharmaceutical composition comprising a compound according to any one of claims 1, 2, 4–7 and 10–16 together with a pharmaceutically acceptable carrier.

18. A composition according to claim 17, which has analgesic activity in mammals.

19. A pharmaceutical composition comprising a compound according to claim 15 together with a pharmaceutically acceptable carrier.

20. A composition according to claim 19, which has analgesic activity in mammals.

21. A pharmaceutical composition comprising a compound according to claim 16 together with a pharmaceutically acceptable carrier.

22. A composition according to claim 21, which has analgesic activity in mammals.

* * * * *

UNITED STATES PATENT AND TRADEMARK OFFICE
CERTIFICATE OF CORRECTION

PATENT NO. : 6,150,355
DATED : November 21, 2000
INVENTOR(S) : Toshiaki Kumazawa, et al.

It is certified that error appears in the above-identified patent and that said Letters Patent is hereby corrected as shown below:

Title page,
Item [57] Abstract,
Line 1, "pharmaceutical" should read -- pharmaceutically --.

Column 4,
Line 59, "Compoung" should read -- Compound --.

Column 6,
Line 4, "5 minutes 10 minutes" should read -- 5 minutes to 10 minutes --.

Column 7,
Line 18, "pasticizer," should read -- plasticizer, --.

Column 10,
Line 63, "2.24 (s, 3H," should read -- 2.24 (s, 3H), --.

Column 11,
Line 47, "6.69 (d, 1H)," should read -- 6.69 (d, 1H, --.

Column 17,
Line 2, "-40phenylpiperidine" should read -- 4-phenylpiperidine --.

Column 18,
Line 31, "-4carboxylate" should read -- 4-carboxylate --.

Column 20,
Line 48, "-4phenylpiperidine" should read -- 4-phenylpiperidine --; and
Line 53, "2methoxymethoxy-6," should read -- 2-methoxymethoxy-6, --.

UNITED STATES PATENT AND TRADEMARK OFFICE
CERTIFICATE OF CORRECTION

PATENT NO. : 6,150,355
DATED : November 21, 2000
INVENTOR(S) : Toshiaki Kumazawa, et al.

It is certified that error appears in the above-identified patent and that said Letters Patent is hereby corrected as shown below:

Column 22,
Line 35, "pharmaceutical" should read -- pharmaceutically --; and
Line 53, "$Ch_2$-O," should read -- $CH_2$-O, --.

Column 24,
Line 3, "10-16" should read -- 8-14 --.

Signed and Sealed this

Sixth Day of November, 2001

Attest:

NICHOLAS P. GODICI
*Attesting Officer*     *Acting Director of the United States Patent and Trademark Office*